United States Patent

Sheehan

[11] Patent Number: 5,885,555
[45] Date of Patent: Mar. 23, 1999

[54] STABILIZED FORMULATIONS OF METHYL SALICYLATE, BICARBONATE ION, AND POLYALKYLENE GLYCOL

[75] Inventor: Craig Sheehan, Belle Mead, N.J.

[73] Assignee: Church & Dwight Co, Inc., Princeton, N.J.

[21] Appl. No.: 99,223

[22] Filed: Jun. 17, 1998

[51] Int. Cl.⁶ .............................. A61K 7/16; A61K 7/20; A23G 3/30
[52] U.S. Cl. .................. 424/49; 424/53; 424/58; 426/651
[58] Field of Search .......................................... 424/49–58

[56] References Cited

U.S. PATENT DOCUMENTS

| | | | |
|---|---|---|---|
| 4,844,883 | 7/1989 | Patel | 424/49 |
| 4,891,211 | 1/1990 | Winston | 424/52 |
| 5,004,596 | 4/1991 | Cocherell et al. | 424/52 |
| 5,085,853 | 2/1992 | Williams et al. | 424/53 |
| 5,128,154 | 7/1992 | Johnson et al. | 426/533 |
| 5,186,926 | 2/1993 | Williams et al. | 424/53 |
| 5,215,740 | 6/1993 | Domek et al. | 424/52 |
| 5,374,368 | 12/1994 | Hauschild | 424/53 |
| 5,425,806 | 6/1995 | Doolan et al. | 424/53 |
| 5,496,542 | 3/1996 | Hauschild | 424/53 |
| 5,676,933 | 10/1997 | Hauschild | 424/53 |

*Primary Examiner*—Shep K. Rose
*Attorney, Agent, or Firm*—Irving Fishman

[57] ABSTRACT

A wintergreen formulation comprising (a) wintergreen; (b) a liquid humectant selected from the group consisting of ethylene oxide/propylene oxide heteric/block copolymers of the formula:

$$HO(C_2H_4O/C_3H_6O)_a(C_2H_4O/C_3H_6O)_bC_2H_4O/C_3H_6O)_c(C_2H_4O/C_3H_6O)_b(C_2H_4O/C_3H_6O)_aH$$

wherein per mole of such copolymer there are a total of about 25 to about 50 moles of ethylene oxide units and about 5 to about 11 moles of propylene oxide units, and said copolymer has a molecular weight of from about 1250 to about 3000; (c) an alkalinity providing agent; and (d) from zero up to no more than 2% water.

18 Claims, No Drawings

STABILIZED FORMULATIONS OF METHYL SALICYLATE, BICARBONATE ION, AND POLYALKYLENE GLYCOL

CROSS-REFERENCE TO RELATED APPLICATIONS

Not Applicable

STATEMENT REGARDING FEDERALLY SPONSORED RESEARCH OR DEVELOPMENT

Not Applicable

1. Field of the Invention

The present invention relates generally to methyl salicylate formulations and their stability in the presence of bicarbonate ions. The invention further relates to the use of polyalkyene glycols as humectants in methyl salicylate formulations in combination with alkaline components. Still further the invention is particularly related to dentrifice formulations having methyl salicylate incorporated therein along with bicarbonate as well as polyalkylene glycol humectants.

2. Background of the Invention

Methyl salicylate (wintergreen) has been used extensively as both a flavor and a pharmaceutically active agent. It has been used as a counter-irritant in many topical formulations, as a flavor in contexts as diverse as antacids, various breath mints, candies, mouthwashes, etc. It is also known that wintergreen degrades in liquid (whether aqueous or not) alkaline environments. Therefore, wintergreen is not truly suitable in the above types of products if an alkaline component is present and even a minor amount of liquid vehicle (especially if water, liquid polyethylene glycol, propylene glycol, and/or glycerin) is present. Wet granulations often supply sufficient water to initiate the degradation process even though the ultimate product (pressed tablet, mint, or candy) appears dry. Other components have sufficient trapped water within their crystal structure which can be released on compression and initiate the degradation. Still other components are hygroscopic to a sufficient degree such that moisture is picked up from the ambient environment in sufficient amounts to initiate the degradation process.

Since wintergreen appears to be acceptable in certain antacid tablets (Tums—calcium carbonate in particular), it appears that perfectly dry solid materials may be suitable for formulating various alkaline compositions with wintergreen as a component. Bicarbonate containing dentrifice formulations have been prepared with various standard humectants such as propylene glycol, glycerin, and polyethylene glycol. Whether or not water is present in these formulations, significant wintergreen degradation is observed when they are flavored with wintergreen. Where water is present, the degradation is more pronounced than when water is absent, but even in the absence of water, wintergreen degradation is still significant with these humectants.

OBJECTS OF THE INVENTION

It is therefore an object of the invention to provide a wintergreen containing alkaline formulation having from no water up to about 1.5% water with improved wintergreen stability.

It is another object of the invention to provide a dentrifice formulation having bicarbonate and wintergreen present where the wintergreen has improved stability over known formulations.

It is yet another object of the invention to provide a wintergreen flavored bicarbonate containing dentrifice formulation with at least 0.75% water present.

Still another object of the invention is to provide a stabilized wintergreen formulation for use in alkaline formulations having up to about 1.5% water.

Still other objects of the invention will be appreciated by those of ordinary skill in the art.

BRIEF SUMMARY OF THE INVENTION

These and other objects of the invention can be achieved by the use of a specialized polyalkylene glycol available from BASF under the name PLURAFLO as a humectant or as a vehicle. With the PLURAFLO in place of the other known liquid humectants, wintergreen can be more stably incorporated into dentrifice (and other) formulations having substantial amounts of alkaline components along with from zero up to 1.5% water.

BRIEF DESCRIPTION OF THE SEVERAL VIEWS OF THE DRAWING

Not Applicable

DETAILED DESCRIPTION OF THE INVENTION

Surprisingly, the objects of the invention are realized by the use of a specialized polyalkyleneglycol available from BASF under the name PLURAFLO® (poloxaflo). More specifically, the specialized polyalkylene glycol is a synthetic copolymer of ethylene and propylene oxide, purposely arranged in both block and heteric fashion. The ethylene oxide weight percent is about 60 to about 95 weight %, preferably about 65 to about 90 weight %, more preferably about 70 to about 85 weight %. Each mole of polymer has from about 25 to about 50 moles, preferably from about 28 to about 48 moles of ethylene oxide units and from about 5 to about 11 moles, preferably 7 to about 9 moles, of propylene oxide. The molecular weight is generally in the range of from about 1250 to about 3000, preferably about 1500 to about 2750, most preferably about 1750 to about 2500. In addition, the specialized polyalkyleneglycol used in the invention generally conforms to general formula I below:

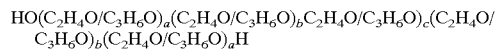

Of particular value in the present invention is poloxaflo 4370.

The poloxaflo is generally used in standard formulations (especially dentrifice formulations) as a replacement for other liquid humectants, particularly liquid polyethylene glycols, liquid pluronics, glycerin, and propylene glycol. While partial replacements of these humectants may be possible without departing from the spirit of the invention, it is preferable that all of these humectants be replaced by the poloxaflo materials set forth herein.

Typically, the poloxaflo used in the present invention is present in amounts in which other liquid humectants typically are used. In dental care products, such amounts range from less than 1% (about 0.06 for tooth powders) to in excess of about 40% for gels and pastes. Particularly preferred amounts include, about 4 to about 6%; about 12 to about 16%; and about 33 to about 36% depending on the type of formulation (powder, paste or gel).

In general, the stabilized formulations contain at least wintergreen, the poloxaflo, an alkalinity source and no more than about 2% water, preferably no more than about 1.5% water, and may contain other components as well. Substantially anhydrous (and totally anhydrous) systems are equally acceptable. The alkalinity source is preferably selected from hydroxides, borates, silicates, sesquicarbonates, percarbonates, carbonates and/or bicarbonates of alkali metals, alkaline earth metals, and/or ammonium ion. In particularly preferred embodiments, the alkalinity source is selected from alkali metal bicarbonates and/or percarbonates. Preferred alkali metal bicarbonates and percarbonates include sodium and potassium bicarbonates and percarbonates. Especially preferred alkalinity sources are sodium percarbonate and sodium bicarbonate. In a most preferred embodiment, sodium bicarbonate is the alkalinity source, while in a second most preferred embodiment sodium bicarbonate and sodium percarbonate are present as alkalinity sources. Another embodiment includes the use of alkaline percarbonate salts as the alkalinity source even in the absence of bicarbonate salts.

Generally, the alkalinity source is present in any amount which may be suitable for the other purposes of the alkalinity providing agent. When present, percarbonate is usually included for the purpose of generating active oxygen when the dentrifice is in use. As such, when percarbonates are present they are usually present in amounts suitable for providing therapeutic levels of active oxygen, although other amounts may be suitable as well. Usually percarbonates, when present in dentifrice products, are utilized in quantities in the range of 2.0 to 4.5% by weight, preferably about 2.5 to about 3.5% by weight. When bicarbonates are present, they are typically present as sodium bicarbonate and usually present from about 5 to about 95 weight %, preferably from about 15 to about 90 weight %, more preferably from about 20 to about 75 weight %, still more preferably from about 25 to about 65 weight %.

In particularly preferred embodiments sodium bicarbonate is present alone or with an alkaline percarbonate (prefereably sodium percarbonate) as the alkalinizing agents. In these embodiments, the sodium bicarbonate is most preferably present as set forth below:

| Type of Dental Care Product | Sodium Bicarbonate |
|---|---|
| Tooth Powder | 90–95% |
| Paste/Gel | 18–24% |
| | 27–30%; |
| | 38–39%; |
| | 48–49%; |
| | 51–52%; |
| | 54–55%; |
| | 59–61%; or |
| | 64–66%. |

In each of the forgoing preferred embodiments, sodium percarbonate may be present or absent, and when present it is typically present in amounts of from 2.5 to 3.5 weight %.

The methyl salicylate used in the present invention is present in typical flavoring useful amounts, which may be incorporated as a pure compound or as a component of a flavoring composition. The methyl salicylate is used in typical flavoring amounts known in the flavoring industry, which may be modified in accordance with general flavoring principles. Preferably, the methyl salicylate can be used in amounts up to about 2.0%, more preferably no more than about 1.2% of the entire final formulation. In preferred embodiments, the methyl salicylate is one component of a flavoring composition which flavoring composition is used in amounts of generally no more than about 2.0%, preferably no more than about 1.2%. When methyl salicylate is one component of a flavoring composition, it may constitute any useful proportion of the flavoring composition, which may vary over wide ranges. Many such formulations are available commercially from a number of sources within the fragrance and flavoring industry. Use of any such methyl salicylate containing flavoring composition is within the scope of the present invention.

The hallmark of the present invention is that methyl salicylate is more stable in alkaline environments when combined with the poloxaflo set forth above than in the absence of the poloxaflo when typical liquid humectants such as liquid polyethylene glycols, liquid pluronics, glycerin, and/or propylene glycol are employed. Retention of the characteristic aroma and taste of methyl salicylate over time in the formulations of the present invention can be utilized as a measure that the stabilization effect has been realized.

In general, in the absence of the poloxaflo required in the present invention, methyl salicylate will degrade in liquid alkaline media (whether or not aqueous in nature) fairly rapidly. When water is present, the degradation will be more pronounced. When more than about 4% water is present, significant degradation will take place even in the presence of the poloxaflo.

As an added measure to increase the stability of the wintergreen, it is preferable to encapsulate it. Spray drying techniques, well known in the art, are particularly preferred. Since the spray drying the wintergreen will phase separate it from the remaining components, the degree of potential interaction and therefore degradation is substantially reduced. Hence, for the most stable products, use of this technique in addition to the use of the poloxaflo in place of the other humectants is the most preferred embodiment for practicing the present invention.

The following examples are provided to exemplify the invention only and are not intended to limit the scope of the invention, which is limited only by the claims.

EXAMPLES

Example 1

Formulations are prepared with the ingredients set forth in Table 1 below, in the amounts set forth. The formulations having polyethylene glycol (PEG)-8 (formulations A and B) are unstable. The compositions containing poloxaflo L4370 (invention formulations C and D) are, by contrast, stable.

TABLE 1

| | Amounts in grams | | | |
|---|---|---|---|---|
| Component | A | B | C | D |
| PEG-8 | 35.0 | 35.0 | 0.0 | 0.0 |
| Poloxaflo L4370 | 0.0 | 0.0 | 35.0 | 35.0 |
| Sodium Bicarbonate | 52.0 | 52.0 | 52.0 | 52.0 |
| Flavor (wintergreen) | 1.2 | 1.2 | 1.2 | 1.2 |
| Water | 0.0 | 1.0 | 0.0 | 1.0 |

The formulations were placed in glass vials and stored at 122° F. for four days, with control samples maintained at room temperature. The samples were then tasted for the presence of wintergreen flavor. Neither sample A nor B were stable, but both of samples C and D were stable.

Example 2

Formulations are prepared with the ingredients set forth in Table 2 below, in the amounts set forth. The formulations having polyethylene glycol (PEG)-8 (formulations E and F)

are unstable. The compositions containing poloxaflo L4370 (invention formulations G and H) are, by contrast, stable. Samples E and F differ from sample A of Example 1 in that Sample E additionally contains sodium saccharin and silica, while Sample F contains both of these and sodium percarbonate as well. Samples G and H differ from Sample C in Example 1 in a parallel fashion.

TABLE 2

| | Amounts in grams | | | |
|---|---|---|---|---|
| Component | E | F | G | H |
| PEG-8 | 35.0 | 35.0 | 0.0 | 0.0 |
| Poloxaflo L4370 | 0.0 | 0.0 | 35.0 | 35.0 |
| Sodium Bicarbonate | 52.0 | 52.0 | 52.0 | 52.0 |
| Flavor (wintergreen) | 1.2 | 1.2 | 1.2 | 1.2 |
| Water | 0.0 | 0.0 | 0.0 | 0.0 |
| Sodium Saccharin | 1.0 | 1.0 | 1.0 | 1.0 |
| Aerosil 200 VS (silica) | 2.0 | 2.0 | 2.0 | 2.0 |
| Sodium Percarbonate | 0.0 | 3.5 | 0.0 | 3.5 |

The formulations were placed in glass vials and stored at 122° F. for four days, with control samples maintained at room temperature. The samples were then tasted for the presence of wintergreen flavor. Neither sample E nor F were stable, but both of samples G and H were stable.

Example 3

Formulation H of Example 2 was repeated except that the poloxaflo L4370 was replaced by an equal weight of propylene glycol, glycerin (99.7%), pluronic L-92, Pluronic L-101, or Pluronic L-121 as set forth in Table 3 below. Neither formulation I nor J were stable and formulations K, L, and M resulted in an unsuitable product for a dentrifice (it gelled in the mouth).

TABLE 3

| | Amounts in grams | | | | |
|---|---|---|---|---|---|
| Component | I | J | K | L | M |
| Propylene Glycol | 35.0 | 0.0 | 0.0 | 0.0 | 0.0 |
| Glycerin (99.7%) | 0.0 | 35.0 | 0.0 | 0.0 | 0.0 |
| Pluronic L-92 | 0.0 | 0.0 | 35.0 | 0.0 | 0.0 |
| Pluronic L-101 | 0.0 | 0.0 | 0.0 | 35.0 | 0.0 |
| Pluronic L-121 | 0.0 | 0.0 | 0.0 | 0.0 | 35.0 |
| Sodium Bicarbonate | 52.0 | 52.0 | 52.0 | 52.0 | 52.0 |
| Aerosil 200 VS (silica) | 2.0 | 2.0 | 2.0 | 2.0 | 2.0 |
| Flavor (wintergreen) | 1.2 | 1.2 | 1.2 | 1.2 | 1.2 |
| Sodium percarbonate | 3.5 | 3.5 | 3.5 | 3.5 | 3.5 |

Example 4

Further example formulations of the invention are as set forth below:

| | Amounts in % | |
|---|---|---|
| Component | N | O |
| Poloxaflo L4370 | 34.110 | 34.475 |
| Pluraflo L1220 Dispersant | 4.000 | — |
| Pluronic F-108 | — | 4.000 |
| Aerosil 200 VS (silica) | 2.000 | 2.000 |
| Sodium Bicarbonate | 50.000 | 48.940 |
| Sodium Saccharin | 1.000 | 1.000 |
| Sodium Fluoride | 0.243 | 0.243 |

-continued

| | Amounts in % | |
|---|---|---|
| Component | N | O |
| Hamposyl L-30 (sodium lauroyl sarcosinate 30%) | 1.677 | 1.675 |
| Sodium Percarbonate | 3.500 | 3.000 |
| Zinc Citrate Trihydrate | 2.000 | — |
| Tetrasodium pyrophosphate | — | 3.060 |
| Sodium Lauryl Sulfate | 0.500 | 0.507 |
| Wintergreen Flavor | 1.100 | 1.100 |

Each of the formulations were tubed and placed on stability at both room temperature and 100° F. After 12 weeks at 100° F. and after 18 months at room temperature there was still a wintergreen taste present. Formulations using polyethylene glycol instead of the poloxaflo indicated in the present invention, result in no wintergreen flavor after storage at room temperature for only 1 week.

I claim:

1. A wintergreen formulation comprising:
   (a) wintergreen;
   (b) a liquid humectant selected from the group consisting of ethylene oxide/propylene oxide heteric/block copolymers of the formula:

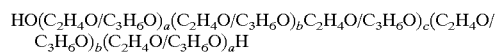

wherein per mole of such copolymer there are a total of about 25 to about 50 moles of ethylene oxide units and about 5 to about 11 moles of propylene oxide units, and said copolymer has a molecular weight of from about 1250 to about 3000;
   (c) an alkalinity providing agent; and
   (d) from zero up to no more than 2% water.

2. The formulation of claim 1 which is a dentrifice.

3. The formulation of claim 2 which is selected from the group consisting of a tooth powder, a toothpaste, and a tooth gel.

4. The formulation of claim 3 wherein component (b) is substantially the only liquid humectant present.

5. The formulation of claim 4 wherein component (b) is the only humectant present.

6. The formulation of claim 3 wherein there is no more than about 1.5% water present.

7. The formulation of claim 6 wherein there is substantially no water present.

8. The formulation of claim 7 which is water-free.

9. The formulation of claim 1 wherein said alkalinity providing agent is selected from the group consisting of hydroxides, borates, silicates, sesquicarbonates, percarbonates, carbonates, bicarbonates, and mixtures thereof of cations selected from the group consisting of alkali metals, alkaline earth metals, ammonium and mixtures thereof.

10. The formulation of claim 9 wherein said alkalinity providing agent is selected from the group consisting of bicarbonates, percarbonates, and mixtures thereof of alkali metals.

11. The formulation of claim 10 wherein said alkalinity providing agent is selected from the group consisting of sodium bicarbonate, sodium percarbonate, and mixtures thereof.

12. The formulation of claim 1 wherein said liquid humectant is a poloxaflo.

13. The formulation of claim 12 wherein said poloxaflo is poloxaflo 4370.

14. A method of improving the stability of wintergreen in a liquid or semi-liquid formulation, which formulation includes an alkalinity providing agent and up to about 2% water, comprising including a liquid humectant selected from the group consisting of ethylene oxide/propylene oxide heteric/block copolymers of the formula:

$$HO(C_2H_4O/C_3H_6O)_a(C_2H_4O/C_3H_6O)_bC_2H_4O/C_3H_6O)_c(C_2H_4O/C_3H_6O)_b(C_2H_4O/C_3H_6O)_aH$$

wherein per mole of such copolymer there are a total of about 25 to about 50 moles of ethylene oxide units and about 5 to about 11 moles of propylene oxide units, and said copolymer has a molecular weight of from about 1250 to about 3000.

15. The method of claim 14 wherein said liquid humectant is substantially the only humectant is said formulation.

16. The method of claim 15 wherein said liquid humectant is the only liquid humectant in said formulation.

17. A preformulation of wintergreen, for use in a liquid or semi-liquid formulation where said formulation has an alkalinity providing agent, said preformulation comprising wintergreen and a liquid humectant selected from the group consisting of ethylene oxide/propylene oxide heteric/block copolymers of the formula:

$$HO(C_2H_4O/C_3H_6O)_a(C_2H_4O/C_3H_6O)_bC_2H_4O/C_3H_6O)_c(C_2H_4O/C_3H_6O)_b(C_2H_4O/C_3H_6O)_aH$$

wherein per mole of such copolymer there are a total of about 25 to about 50 moles of ethylene oxide units and about 5 to about 11 moles of propylene oxide units, and said copolymer has a molecular weight of from about 1250 to about 3000.

18. The preformulation of claim 17 further comprising at least one of (a) an additional flavoring component and (b) a wintergreen flavoring acceptable vehicle.

* * * * *